United States Patent [19]

Ryu et al.

[11] 4,061,689

[45] Dec. 6, 1977

[54] PROCESS FOR THE CONVERSION OF AROMATIC HYDROCARBONS

[75] Inventors: Ji-Yong Ryu; Dalia Germanas, both of Des Plaines, Ill.

[73] Assignee: UOP Inc., Des Plaines, Ill.

[21] Appl. No.: 644,785

[22] Filed: Dec. 29, 1975

[51] Int. Cl.² ............................................. C07C 3/56
[52] U.S. Cl. ........................... 260/671 R; 252/441; 260/671 C; 260/671 P
[58] Field of Search ........... 260/671 R, 671 C, 671 P; 252/441

[56] References Cited

U.S. PATENT DOCUMENTS

| | | | |
|---|---|---|---|
| 2,951,885 | 9/1960 | Wade | 260/671 C |
| 2,965,686 | 12/1960 | Prill | 260/671 C |
| 2,999,074 | 9/1961 | Bloch et al. | 252/441 |
| 3,402,213 | 9/1968 | Rosset | 260/671 R |

*Primary Examiner*—Delbert E. Gantz
*Assistant Examiner*—C. E. Spresser
*Attorney, Agent, or Firm*—James R. Hoatson, Jr.; Richard D. Stone; William H. Page, II

[57] ABSTRACT

A process for the converting of aromatic hydrocarbons, e.g., reacting an alkylating agent, preferably an olefin, with an aromatic hydrocarbon. The process uses a catalyst prepared by reducing, with hydrogen gas at an elevated temperature, titanium tetrafluoride on an inorganic oxide which contained surface hydroxyl groups.

12 Claims, No Drawings

PROCESS FOR THE CONVERSION OF AROMATIC HYDROCARBONS

BACKGROUND OF THE INVENTION

1. Field of the Invention

The present invention relates to an improved process for the conversion of an aromatic hydrocarbon in the presence of a titanium subfluoride on an inorganic oxide catalyst.

The invention is described with reference to alkylation, e.g., the synthesis of ethylbenzene or cumene by alkylation of benzene with ethylene or propylene in the presence of the catalyst. The invention can also be used in alkylaromatic transalkylation and isomerization.

2. Description of the Prior Art

Conversion of aromatic hydrocarbons is well known in industry. Some of the aromatic conversion reactions which occur include alkylation of aromatic hyrocarbons with an alkylating agent such as an olefin, disproportionation or transalkylation of alkyl aromatics and isomerization of alkyl aromatics such as xylenes, and of dialkyl and higher substituted aromatics.

Of special interest, has been the alkylation of benzene to ethylbenzene, or cumene. Ethylbenzene may be dehydrogenated to make styrene, while cumene is used for the production of phenol and acetone. Cumene is also dehydrogenated to form methylstyrene, in a process similar to that used to convert ethylbenzene to styrene. Ethylbenzene and cumene may also be used as blending components in aviation gasoline because of their high octane number.

It is well known that cumene can be synthesized from benzene and propylene using a catalyst of $AlCl_3$, SPA or $BF_3$. SPA is a generally accepted abreviation for solid phosphoric acid catalyst, or phosphoric acid which is adsorbed on kieselguhr or other support.

Ethylbenzene can be synthesized from benzene and ethylene using $AlCL_3$ but SPA is not used commercially for this purpose. $AlCl_3$ is a very popular alkylation catalyst, because of its high activity. Unfortunately, the catalyst operates as a slurry or sludge which is messy to handle on a commercial scale, and also is corrosive. The highly reactive nature of this Friedel-Crafts metal halide catalyst, $AlCl_3$, is desirable when attempting to alkylate benzene with ethylene, because less active catalyst systems do not work.

Another highly selective catalyst system has been developed for the alkylation of benzene with olefins. This catalyst comprises boron trifluoride. The boron trifluoride catalyst system is exceptionally active and permits operation with dilute olefin streams, but it requires the continuous addition of $BF_3$ to maintain catalyst activity. High catalyst activity also leads to oligomerization of olefins so that the contact time of olefins with $BF_3$ catalyst should be as short as possible. This catalyst is also exceptionally water sensitive, as water not only destroys the catalyst, but produces very corrosive solutions which attack downstream processing units. $BF_3$ also frequently appears in the product, and must be removed therefrom.

Because of the interest in alkylating benzene with olefins, and because of the inadequacies of existing catalyst systems, we studied the work that others and done, and made exhaustive investigations to determine if it would be possible to find a catalyst which would have the activity and selectivity required to produce an acceptable product, while making maximum use of existing petroleum resources.

A highly active catalyst was sought, to permit operation at lower temperatures with less utility cost, cost of construction, and to operate with less catalyst. In new units this would mean smaller, and cheaper reactor vessels, while in existing units it would mean that an increase in capacity could be obtained by changing catalyst in an existing reactor vessel with minor modification.

High selectivity is necessary, not only to permit operation with feedstreams which are not 100% pure olefin, but also to maximize production of the desired product, and to minimize production of polymerized olefins, or polyalkylated aromatic compounds.

Accordingly, many catalyst systems were studied to find a catalyst with excellent activity and selectivity, which was not corrosive or destroyed by water.

There has been extensive work done with Ti catalysts, though most work occurred in conjunction with studies of Ziegler-Natta catalysts. The closest prior art known in U.S. Pat. No. 2,381,481 (Class 260–683.15), U.S. Pat. No. 2,951,885 (Class 260–671), U.S. Pat. No. 2,965,686 (Class 260–671) and U.S. Pat. No. 3,153,634 (Class 252–429).

In U.S. Pat. No. 2,381,481, preparation and use of a catalyst prepared by treating alumina gel with fluotitanic acid is disclosed. This catalyst is used for polymerization of olefins to heavier hydrocarbons, and also for alkylation of parafins with olefins, the latter when operating at high temperatures, between 700° and 900° F. or higher. No mention is made of alkylation of aromatics with olefinic hydrocarbons or transalkylation of polyalkylbenzenes.

In U.S. Pat. No. 2,951,885, there is disclosed the use of titanium trihalide on activated alumina or other activated acidic oxide for alkylation of benzene with olefins. The catalyst is originally a tetrachloride, subsequently reduced to the trichloride with an alkali metal such as sodium, lithium, or potassium. The examples show that this catalyst will alkylate benzene with ethylene.

In U.S. Pat. No. 2,965,686, the thrust of the application was to develop a titanium subchloride catalyst. The subchloride catalyst was prepared by reacting titanium metal, in the form of turnings, with titanium tetrachloride. The patentee speculated, but gave no examples, showing that it would be possible to form the subchloride by reduction of titanium tetrachloride with hydrogen. The patentee did not believe the difficulties to be encountered would justify reduction of hydrogen.

In U.S. Pat. No. 3,153,634, there is disclosed the use of titanium subhalides in a polymerization reaction. The patentee is probably describing catalyst to make solid polymer, as he discusses production of solid polymer products. The patentee seems to teach that the halides all act equivalently. The patentee in U.S. Pat. No. 3,153,634 taught the very antithesis of applicants process, on page 3 lines 65–75 where he mentions use of benzene as an inert solvent to hold dissolved olefins, rather than as a reactant.

Accordingly, work continued on developing an improved process for the catalytic conversion of aromatic hydrocarbons.

SUMMARY OF THE INVENTION

Accordingly, the present invention provides a process for the catalytic conversion of an aromatic hydrocarbon comprising contacting the aromatic hydrocarbon with a reactant in the presence of a catalyst prepared by reacting a titanium tetrafluoride with a support which contains surface hydroxyl groups and reducing with hydrogen at an elevated temperature, to form titanium subfluoride, and recovering a converted aromatic hydrocarbon as a product of the process.

DETAILED DESCRIPTION

The catalyst of the present invention comprises a titanium subfluoride on a suitable support containing surface hydroxyl groups, preferably a Group III-A metal oxide. The support must contain hydroxyl groups which will react with the titanium component. Once the titanium tetrachloride is supported on the support, it is reduced with hydrogen to form the subhalide. The Group III-A metal oxides possess the necessary surface hydroxyl groups.

Specific examples of the Group III-A metal oxides which possess surface hydroxyl groups and which also possess a relatively high surface area include alumina, gallium oxide, indium oxide, and thallium oxide. Of these compounds, the preferred support is alumina, and especially low density, high surface area aluminas such as gamma-alumina or, if so desired, eta-alumina.

The apparent bulk density of the alumina is preferably 0.3 to 0.8 g/cm$^3$, with a surface area of 1 to 500 m$^2$/g. The alumina may be in any shape, e.g., spheroidal alumina, as prepared by the well known oil-drop method. The alumina may be treated to provide greater physical stability, e.g., impregnated with a compound such as barium nitrate, which upon calcination is converted into barium oxide.

A commercial gamma-alumina may also be used as the support. Since this commercial gamma-alumina could contain an excessive amount of water which would consume an excess of titanium tetrahalide without any beneficial effect on the catalyst, in the preferred embodiment of this invention, the commercial gamma-alumina is subjected to a predrying step by heating to 300° to 600° C in inert gas or hydrogen flow for 1 to 10 hours. This predrying step is used when preparing a catalyst using the sublimation method or when using an impregnation method using a titanium tetrafluoride solution in organic solvents. However, if the catalyst is prepared by using an aqueous titanium hexafluoric acid as the impregnating agent, the commercial gamma-alumina can be used without predrying.

If the catalyst is further supported on an inert carrier, any well known inert supports can be used. These include silica, clays, charcoal, gravel, sand, etc., though all of these will not give equivalent results.

It is also within the scope of the present invention to add one or more promoters to the catalyst system. It is believed that use of one or more promoters, e.g., Group VIII and Group VI-B metals, may be beneficial to the practice of the present invention.

When it is desired to use the catalyst system in an alkylaromatic isomerization process, then alkylaromatic isomerization reaction conditions should be used. Reaction conditions are disclosed in U.S. Pat. No. 3,637,881 (Class 260–688a), the teachings of which are incorporated by reference. When it is desired to use the catalyst system of the present invention for alkylaromatic transalkylation, then appropriate reaction conditions should also be used. These are disclosed in U.S. Pat. No. 3,720,726 (Class 260–672t), the teachings of which are incorporated by reference. Reaction conditions for the alkylation of aromatic hydrocarbons will be discussed in detail in a latter part of this specification.

Two different catalyst preparation techniques may be used, sublimation an impregnation.

In one sublimation procedure titanium tetrafluoride may be placed on top of a bed of gamma-alumina. Preferably the alumina is predried at 300° to 600° C for 1 to 10 hours under hydrogen or nitrogen flow to activate the alumina and desorb all water therefrom. Drying should not be so severe to remove the surface hydroxyl groups necessary for an active catalyst. Non-predried, commercial alumina may also be used but there will be a significant loss of TiF$_4$ to titanium oxide or titanium oxyfluoride. The titanium tetrafluoride and alumina should be maintained in a dry, inert atmosphere, after drying. While passing nitrogen downflow over the mixture of alumina and titanium tetrafluoride, the temperature is slowly increased to a temperature slightly above the sublimation temperature of titanium tetrafluoride, 284° C, then the temperature is increased, to higher temperatures. Temperature as high as 700° C may be used in this step. Heat treatment at higher temperatures may be omitted. Following this, the titanium is reduced to a lower oxidation state than +4 by treatment with flowing hydrogen at 400° to 700° C.

Another sublimation technique is to mix the titanium tetrafluoride with a desired amount of substrate and heat the mixture to a temperature in excess of 300° C in an inert gas such as nitrogen, or if so desired, in hydrogen gas. Following this, the reduction of the titanium to a valence state of less than +4 is effected in a manner similar to that hereinbefore set forth. Upon completion of the final treatment, the finished catalyst should be sealed under a dry, inert atmosphere.

Another way to prepare catalyst for use in the present invention is to impregnate the support with a solution containing a compound which will decompose to form titanium tetrafluoride. A preferred titanium tetrafluoride impregnating solution consists of an organic polar solvent solution or aqueous solution of TiF$_4$ in water, or an aqueous solution of M$_2$MiF$_6$, where M equals H, Li, Na, or K. In all impregnating methods is is preferred to contact the support with impregnating solution at room temperature and then progressively increase the temperature to evaporate the solvent. The catalyst is then preferably heated to 200° to 600° C under an inert atmosphere and then reduced with hydrogen at 400° to 700° C. The catalyst should be stored in a dry, inert atmosphere.

Unfortunately, the sublimation procedure required excess amounts of titanium compounds to insure that all parts of the support are contacted by titanium compounds. Because of the difficulties encountered with this procedure, the impregnation route is much preferred. In impregnation, it is of course possible to vary over a wide range the concentration of titanium compound in the finished catalyst system. At least about 0.5 weight percent titanium is believed necessary for a significant amount of catalytic effect to occur. The upper limit on titanium is believed to be about 20%.

The ratios of reactants and other reaction conditions which occur when alkylating benzene with light olefins are basically those well known in the art. It is desirable to maintain pressures high enough to have a liquid phase in the reaction zone. Preferred pressure seems to be around 20 to 60 atm, with an optimum pressure of about 35 atm.

Temperature effects the conversion of olefins. Temperature may range between ambient and 250° C. At very low temperatures, the catalyst is not sufficiently active to permit the desired reaction to proceed at a satisfactory rate. At very high temperatures, it is believed that the catalyst may be damaged by formation of carbonaceous materials on the catalyst.

Preferred operating temperatures seem to be about 100° to 200° C. It is difficult to pick an optimum temperature, but this may be because conversion of olefins is so high. Further studies, with less conversion, may indicate an optimum temperature for this reaction.

The catalyst may be disposed in a reactor vessel as a fixed, fluidized or moving bed of catalyst. The reactants may contact the catalyst in upflow, downflow or cross-flow fashion, though upflow of reactants over a fixed bed of catalyst is preferred.

The liquid hourly space velocity in the reactor may range from 0.1 to 20. Because catalyst of the present invention is very active for the alkylation reaction, significantly higher space velocities are possible than when using some prior art catalysts, e.g., SPA. To some extent, the liquid hourly space velocity is related to temperature in the reaction zone, in general, a higher LHSV will require higher temperature operation.

The catalyst of the present invention has a number of advantages over SPA. SPA is a very poor catalyst for alkylation of benzene with ethylene, but is satisfactory for alkylation with propylene. The alkylation of benzene with propylene over SPA is only economically feasible at high benzene to propylene ratios. With high ratios (about 8 to 1 molar), cumene is produced in high yields, with very little production of polyalkylated species. Production of di- and tri-alkylated species must be minimized because SPA does not catalyze transalkylation, so the polyalkylated species must be discarded. The process of the present invention permits alkylation of an aromatic with ethylene, propylene, or heavier olefins. Any polyalkylated species formed can be recycled and transalkylated to the desired product, in the same or a separate reactor containing the catalyst of the present invention. The catalyst used in the process of the present invention is slightly less active than either $BF_3$ or $AlCl_3$ for transalkylation or alkylation of benzene with ethylene. However, the process of the present invention does not have the corrosion problems associated with $BF_3$ and $AlCl_3$. Further, at slightly higher temperatures, the titanium subfluoride catalyst used in the process of the present invention can do the same job as $BF_3$ or $AlCl_3$, without the headaches of $BF_3$ addition or sludge reactors. For alkylation of aromatics with higher molecular weight olefins, e.g., propylene, and heavier olefins, $BF_3$ and $AlCl_3$ are too active and produce polyalkylated species. $BF_3$ and $AlCl_3$ are also too acidic to be good transalkylation catalysts, causing at times more dealkylation than alkyl transfer.

Accordingly, one of the outstanding advantages of the process of the present invention is that it is capable of both alkylating and transalkylating propyl groups, and even higher molecular weight alkyl groups. This is a distinct commercial advantage in that it permits a refiner to operate his alkylation reactor at, e.g., lower benzene to propylene ratios. Benzene to propylene ratios of around 3 are believed to be optimum when the process of the present invention is applied to the benzene recycle will be required. In addition, the polyalkylated species produced can be transalkylated with benzene to produce more cumene, with practically complete elimination of any disposal of polyalkylated species.

The catalyst used in the process of the present invention is also believed to have excellent characteristics for a detergent alkylation process. It should be possible to alkylate benzene with olefins having a carbon chain length of 5 to 20, and preferably 8 to 16. In the past, HF acid has been used to catalyze the alkylation reaction wherein benzene contacts the olefin in the presence of liquid HF acid, which is very corrosive. $AlCl_3$ and $BF_3$ are not believed suitable for the production of detergent alkylate, because as hereinbefore mentioned, they are too active and produce polyalkylated species.

EXAMPLE I

An aqueous solution of titanium hexafluoric acid was used to impregnate gamma-alumina. The alumina was 1.6 mm spheres, with an ABD of 0.52. 300 cc (156.6 g) of alumina was impregnated with 250 ml of the aqueous solution which contained 10 cc of 60% $H_2TiF_6$. After impregnation, the impregnation product was placed in a pyrex glass reaction vessel and treated as follows:

|  | Stage One | Stage Two | Stage Three |
| --- | --- | --- | --- |
| T, °C | 140 | 300 | 550 |
| Hours | 1 | 2.5 | 3.0 |
| Gas | $N_2$ | $N_2$ | $H_2$ |
| Flow, cc/min | 1500 | 1500 | 1500 |

This was catalyst A. It contained 1.32 wt. % Ti and 4.2 wt. % F.

This catalyst, 50 cc (25.3 g) was loaded into a 0.78 inch I.D. stainless steel. Benzene and ethylene, in a mole ratio of 8:1, were passed upflow through the reactor at 170 C, 200 psig., and 4.0 LHSV. The liquid product contained:

| Component | Wt. % |
| --- | --- |
| Non-Aromatics | 0.2 |
| Benzene | 86.5 |
| Ethylbenzene | 7.0 |
| Diethylbenzene | 1.4 |
| Triethylbenzene | 0.4 |
| Butylbenzene | 2.2 |

EXAMPLE II 325 cc (169 g) of 1.6 mm diameter gamma-alumina spheres which possessed an ABD of 0.52 was impregnated in a steam rotary drier with a solution of 10 ml (16.99 g) of 60% $H_2TiF_6$ diluted to 350 ml with de-ionized water. The impregnation product was subjected to the following treatments:

|  | Stage One | Stage Two | Stage Three |
| --- | --- | --- | --- |
| T, °C | 140 | 300 | 550 |
| Hours | 1 | 1.5 | 3 |
| Gas | $N_2$ | $N_2$ | $H_2$ |
| Flow, cc/min | 800 | 800 | 1000 |

The finished catalyst contained 1.74 wt. % Ti and 3.7 wt. % F. A 50 cc sample weighed 26.38 g.

This sample of catalyst was loaded into a vertical tubular (I.D. = 1.25 inch) glass reactor in a heating means. Ethylbenzene vapor was passed downflow over the catalyst. Ethylbenzene flows were 26.1 g/100 min at 200 C, and 23.6 g/100 min at 250 C under atmospheric pressure. Helium ws continuously added at the rate of 10 cc/min, as measured. The liquid product was collected in an ice bath. The liquid product contained:

| Component | Weight Percent At 200 C | Weight Percent At 250 C |
|---|---|---|
| Non-Aromatics | 0.1 | 0.1 |
| Benzene | 2.2 | 3.6 |
| Toluene | 0.5 | 0.3 |
| Ethylbenzene | 94.1 | 90.1 |
| 1,3 DEB | 1.8 | 3.7 |
| 1,4 DEB | 1.2 | 1.8 |
| 1,2 DEB | 0.1 | 0.4 |

EXAMPLE III

For comparison purposes, the transalkylation activity of $BF_3$ catalyst was tested. This catalyst, $BF_3$ supported on alumina, was loaded into the same reactor used in reactor 2. Ethylbenzene vapor was passed under atmospheric pressure downflow over the catalyst at 14.9 g/100 min at 200° C with He flow of 10 cc/min. The liquid product contained:

| Component | Wt. % |
|---|---|
| Non-Aromatics | — |
| Benzene | 1.1 |
| Toluene | 0.1 |
| Ethylbenzene | 96.8 |
| 1,3 DEB | 1.1 |
| 1,4 DEB | 0.8 |
| 1,2 DEB | 0.1 |

Thus, even at lower flow rates the $BF_3$ did not possess the transalkylation activity of catalyst of the present invention.

EXAMPLE IV

Catalyst of the present invention was prepared by impregnating 325 cc of 1.6 mm diameter gamma-alumina spheres with a solution prepared by diluting 30 ml (49.01 g) of 60% $H_2TiF_6$ to 350 ml with de-ionized water. The alumina and impregnating solution were placed in a steam rotary drier. The materials were contacted for 20 minutes with rotation of the drier, but without steam. Steam was then admitted to the steam jacket of the drier and the solution evaporated to dryness with rotation of the drier. The impregnated material was then subjected to the following treatment:

| | Stage One | Stage Two | Stage Three |
|---|---|---|---|
| T °C | 140 | 300 | 550 |
| Hours | 1.0 | 1.67 | 3.0 |
| Gas | $N_2$ | $N_2$ | $H_2$ |
| Flow, cc/min | 800 | 800 | 800 |

The finished catalyst contained 5.37 wt. % Ti and 6.8 wt % F.

This catalyst was tested for its ability to catalytically convert cumene. The feed to the unit was a dried, technical grade cumene, with the following analysis:

| Ethylbenzene | 0.4 |
|---|---|
| Cumene | 99.0 |
| n-Propylbenzene | 0.1 |
| $C_9$ Aromatics | 0.5 |

This material was passed upflow over 50 cc (28.78 g) of the catalyst at varying reaction conditions. The results are reported in the following table. The pressure was held constant at 35 atm, absolute.

| Period | Hours On Stream | Temp °C | LHSV | Plant PSIG | Non-Aromatic | Benzene | Unknown | Isopropyl-Benzene | Unknown | Di-isopropyl-Benzene | Unknown | Ethylbenzene |
|---|---|---|---|---|---|---|---|---|---|---|---|---|
| 1 | 5–9 | 140 | 4 | 500 | 0.1 | 12.0 | 0.1 | 63.5 | 0.4 | 22.6 | 1.0 | 0.3 |
| 2 | 9–13 | 140 | 4 | 500 | 0.1 | 12.5 | — | 62.5 | 0.3 | 23.3 | 1.0 | 0.3 |
| 4 | 13–17 | 140 | 4 | 500 | 0.1 | 12.5 | — | 62.8 | 0.3 | 23.0 | 1.0 | 0.3 |
| 7 | 33–37 | 140 | 2 | 500 | 0.2 | 14.9 | 0.1 | 55.2 | 0.4 | 27.3 | 1.6 | 0.3 |
| 11 | 53–57 | 120 | 2 | 500 | 0.1 | 8.3 | — | 73.6 | 0.7 | 16.5 | 0.5 | 0.3 |
| 15 | 73–77 | 120 | 4 | 500 | — | 6.3 | — | 80.7 | 0.1 | 12.6 | tr | 0.3 |
| 19 | 89–93 | — | — | — | — | 5.9 | — | 82.6 | 0.1 | 11.1 | tr | 0.3 |
| 20 | 97–101 | 140 | 4 | 500 | 0.1 | 12.1 | — | 63.9 | 0.1 | 23.5 | 0.1 | 0.2 |
| 24 | 113–117 | — | — | — | 0.1 | 11.2 | — | 66.2 | 0.1 | 22.1 | 0.1 | 0.2 |
| 25 | 121–125 | 140 | 1 | 500 | 0.2 | 15.4 | — | 53.4 | 0.6 | 30.0 | 0.1 | 0.3 |
| 27 | 133–137 | — | — | — | 0.2 | 16.0 | — | 52.8 | 0.2 | 30.3 | 0.3 | 0.2 |

All Analyses Are Given In Weight Percent

We claim as our invention:

1. A process for the alkylation of an aromatic hydrocarbon comprising contacting the aromatic hydrocarbon with an alkylating agent at aromatic hydrocarbon alkylation conditions in the presence of a catalyst prepared by reacting titanium tetrafluoride with a support which contains surface hydroxyl groups and thereafter reducing with hydrogen at an elevated temperature to form titanium subfluoride, and recovering an alkylated aromatic hydrocarbon as a product of the process.

2. The process of claim 1 wherein the catalyst is prepared by impregnating the support with a solution of $TiF_4$, drying in an inert atmosphere at 200° to 600° C, and then reducing with hydrogen at 400° to 700° C.

3. The process of claim 2, wherein the impregnating solution used is selected from the group consisting of an aqueous solution of $TiF_4$, polar organic solvent solutions of $TiF_4$, and aqueous solutions of $M_2TiF_6$ where M is H, Li, Na or K.

4. The process of claim 1 wherein the catalyst is prepared by subliming $TiF_4$ in a carrier gas and contacting the gas and $TiF_4$ with the support at a temperature of 284° to 700° C, then reducing with hydrogen at 400° to 700° C.

5. The process of claim 1 wherein, prior to reduction, the catalyst is given a thermal pre-treatment at 100 to 200° C for one-half to 2 hours, then at 250° to 350° C for one-half to 2 hours, and then at 400° to 600° C for one to 10 hours.

6. The process of claim 1 wherein the support is a Group III-A metal oxide.

7. The process of claim 6 wherein the support is alumina having an apparent bulk density of 0.3 to 0.8 gm/cm³ and a surface area of 1 to 500 m²/g.

8. The process of claim 6 wherein the Group III-A metal oxide is selected from the group of oxides of aluminum gallium and indium.

9. The process of claim 1 wherein the catalyst contains, on an elemental basis, about 0.5 to 20 weight percent titanium.

10. The process of claim 1 wherein the aromatic hydrocarbon is selected from the group consisting of benzene, toluene, ethylbenzene, xylene and cumene isomers.

11. The process of claim 1 wherein benzene is alkylated with an olefin selected from the group consisting of ethylene and propylene.

12. The process of claim 1 wherein benzene is alkylated with an olefin selected from the group consisting of $C_8$ to $C_{18}$ olefins.

* * * * *